United States Patent
Lee (10) Patent No.: US 8,915,855 B2
(45) Date of Patent: Dec. 23, 2014

(54) ULTRASOUND SYSTEM AND METHOD FOR PROVIDING MULTIPLE PLANE IMAGES FOR A PLURALITY OF VIEWS

(75) Inventor: Yun Hee Lee, Seoul (KR)

(73) Assignee: Samsung Medison Co., Ltd., Hongcheon-gun, Gangwon-do (KR)

( * ) Notice: Subject to any disclaimer, the term of this patent is extended or adjusted under 35 U.S.C. 154(b) by 354 days.

(21) Appl. No.: 12/875,024

(22) Filed: Sep. 2, 2010

(65) Prior Publication Data

US 2011/0054324 A1 Mar. 3, 2011

(30) Foreign Application Priority Data

Sep. 3, 2009 (KR) .................. 10-2009-0083074

(51) Int. Cl.
*A61B 8/00* (2006.01)
*G01S 15/89* (2006.01)
*A61B 8/08* (2006.01)
*G01S 7/52* (2006.01)

(52) U.S. Cl.
CPC ........... *G01S 15/8993* (2013.01); *A61B 8/0808* (2013.01); *A61B 8/0866* (2013.01); *A61B 8/523* (2013.01); *G01S 7/52063* (2013.01)
USPC .......................................... 600/443; 600/444

(58) Field of Classification Search
USPC ............... 600/437, 443, 444, 445; 702/19
See application file for complete search history.

(56) References Cited

U.S. PATENT DOCUMENTS

| | | | |
|---|---|---|---|
| 7,783,095 B2* | 8/2010 | Carneiro et al. | ............ 382/128 |
| 8,083,678 B2 | 12/2011 | Abuhamad | |
| 8,447,090 B2 | 5/2013 | Wakai et al. | |
| 2003/0097219 A1* | 5/2003 | O'Donnell et al. | ............ 702/19 |
| 2004/0210138 A1 | 10/2004 | Murashita et al. | |
| 2005/0101855 A1 | 5/2005 | Miga et al. | |
| 2005/0251036 A1 | 11/2005 | Abuhamad | |
| 2005/0283079 A1* | 12/2005 | Steen et al. | ............ 600/447 |
| 2006/0034513 A1 | 2/2006 | Cai et al. | |
| 2007/0081705 A1 | 4/2007 | Carneiro et al. | |

(Continued)

FOREIGN PATENT DOCUMENTS

| | | |
|---|---|---|
| JP | 2003-523794 | 8/2003 |
| JP | 2004-313651 | 11/2004 |

(Continued)

OTHER PUBLICATIONS

Fratelli et al., "An introduction to fetal neurosonography using three-dimensional ultrasound", Philips, 2007, pp. 1-12.*

(Continued)

*Primary Examiner* — Christopher Cook
(74) *Attorney, Agent, or Firm* — McDermott Will & Emery LLP (57) ABSTRACT

Embodiments for forming multiple plane images for a target object in an ultrasound system are disclosed. A processor forms volume data indicative of the target object by using ultrasound data. The processor is configured to: set a reference plane in the volume data; detect a falx contour and a contour of a cerebrum in the reference plane and an entire contour of the brain in the volume data; normalize the volume data by using the falx contour, the cerebrum contour and the entire contour of the fetal brain; and set multiple planes with respect to the reference plane in the volume data. The processor forms plane images corresponding to the respective multiple planes by using the volume data.

15 Claims, 6 Drawing Sheets

(56) References Cited

U.S. PATENT DOCUMENTS

| | | |
|---|---|---|
| 2007/0167779 A1 | 7/2007 | Kim et al. |
| 2007/0249935 A1 | 10/2007 | Deschinger et al. |
| 2008/0051653 A1 | 2/2008 | Choi et al. |
| 2008/0262344 A1 | 10/2008 | Brummett |
| 2009/0093717 A1* | 4/2009 | Carneiro et al. ............. 600/443 |
| 2010/0217123 A1* | 8/2010 | Eran et al. .................... 600/437 |

FOREIGN PATENT DOCUMENTS

| | | |
|---|---|---|
| JP | 2006-502776 | 1/2006 |
| JP | 2006-208250 A | 8/2006 |
| JP | 2006-314778 A | 11/2006 |
| JP | 2007-289685 A | 11/2007 |
| JP | 2008-49158 A | 3/2008 |
| JP | 2008-183063 | 8/2008 |
| JP | 2008-534082 A | 8/2008 |
| JP | 2009-28515 A | 2/2009 |
| JP | 2009-39446 A | 2/2009 |
| KR | 10-2007-0039232 | 4/2007 |
| WO | WO 01/32258 A2 | 5/2001 |
| WO | WO 2004/035135 A1 | 4/2004 |

OTHER PUBLICATIONS

Korean Office Action issued in Korean Patent Application No. KR 10-2009-0083074 dated Oct. 11, 2011.

"Sonographic Examination of the Fetal Central Nervous System: Guidelines for Performing the 'Basic Examination' and the "Fetal Neurosonogram"", Ultrasound in Obstetrics and Gynecology, vol. 29, No. 1, (Jan. 1, 2007) pp. 109-116.

European Search Report dated Oct. 22, 2012.

Japanese Notice of Allowance issued in Japanese Patent Application No. 2010-197890 issued Apr. 8, 2014, with English Translation.

* cited by examiner

ULTRASOUND SYSTEM AND METHOD FOR PROVIDING MULTIPLE PLANE IMAGES FOR A PLURALITY OF VIEWS

CROSS-REFERENCE TO RELATED APPLICATIONS

The present application claims priority from Korean Patent Application No. 10-2009-0083074 filed on Sep. 3, 2009, the entire subject matter of which is incorporated herein by reference.

TECHNICAL FIELD

The present disclosure generally relates to ultrasound systems, and more particularly to an ultrasound system and a method of providing multiple plane images for a plurality of views.

BACKGROUND

An ultrasound system has become an important and popular diagnostic tool since it has a wide range of applications. Specifically, due to its non-invasive and non-destructive nature, the ultrasound diagnostic system has been extensively used in the medical profession. Modern high-performance ultrasound diagnostic systems and techniques are commonly used to produce ultrasound images of internal features of an object (e.g., human organs).

Recently, the ultrasound system may provide a 3-dimensional ultrasound image showing clinical information such as spatial information, anatomical features and the like, which may not be provided through a 2-dimensional ultrasound image. To provide the 3-dimensional ultrasound image, the ultrasound system may transmit/receive ultrasound signals to/from a target object to form volume data. It may then perform rendering upon the volume data to thereby form the 3-dimensional ultrasound image of the target object.

Also, the ultrasound system may provide multiple plane images corresponding to a plurality of views for diagnosis of the target object (e.g., fetal brain). For example, the ultrasound system may provide plane images corresponding to a transthalamic plane, a transventicular plane and a transcerebellar plane associated with an axial view, plane images corresponding to a transthalamic plane, a transcerebellar plane, a transcaudate plane and a transfrontal plane associated with a coronal view, and plane images corresponding to a midsagittal plane, a left parasagittal plane and a right parasagittal plane associated with a sagittal view.

Conventionally, the multiple planes for the respective axial view, coronal view and sagittal view may be manually defined in the volume data. Thus, since it may be difficult to accurately define the corresponding planes in the volume data, desirable plane images may not be provided and a relatively long time to obtain the multiple plane image may be consumed.

SUMMARY

Embodiments of providing multiple plane images for a plurality of views in an ultrasound system are disclosed herein. In one embodiment, by way of non-limiting example, an ultrasound system includes: an ultrasound data acquisition unit configured to transmit/receive ultrasound signals to/from a target object including a brain to form ultrasound data; and a processor configured to form volume data indicative of the target object by using the ultrasound data. The processor includes: a first plane setting section operable to set a reference plane in the volume data; a contour detecting section operable to detect a falx contour and a contour of a cerebrum in the reference plane and an entire contour of the brain in the volume data; a preprocessing section operable to normalize the volume data by using the falx contour, the cerebrum contour and the entire contour of the brain; and a second plane setting section operable to set multiple planes with respect to the reference plane in the volume data, wherein the processor is further operable to form plane images corresponding to the respective multiple planes by using the volume data.

In one embodiment, a method of providing multiple plane images for a target object including a brain in an ultrasound system, comprises: a) forming volume data indicative of a target object including a brain; b) setting a reference plane in the volume data; c) detecting a falx contour and a contour of a cerebrum in the reference plane and an entire contour of the brain in the volume data; d) normalizing the volume data by using the falx contour, the cerebrum contour and the entire contour of the brain; e) setting multiple planes with respect to the reference plane in the volume data; and f) forming plane images corresponding to the respective multiple planes by using the volume data.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
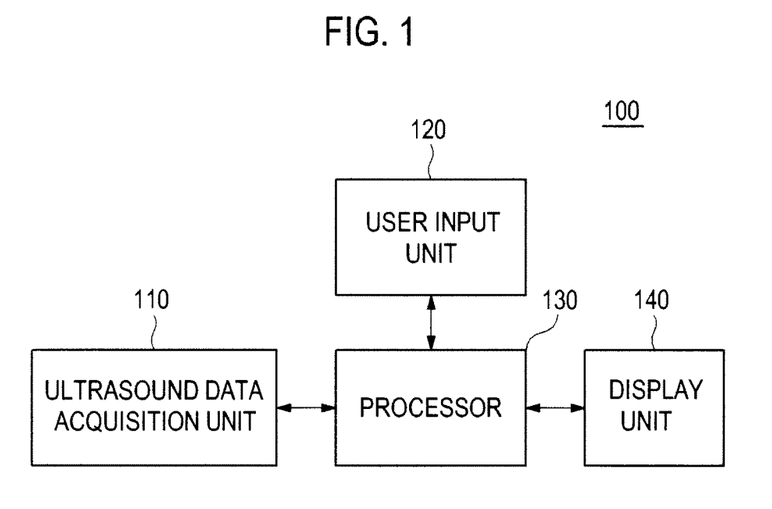
FIG. 1 is a block diagram showing an illustrative embodiment of an ultrasound system.

FIG. 1 is a block diagram showing an illustrative embodiment of an ultrasound system. The ultrasound system 100 may include an ultrasound data acquisition unit 110, a user input unit 120, a processor 130 and a display unit 140.

The ultrasound data acquisition unit 110 may be operable to transmit ultrasound signals to a target object and receive ultrasound signals reflected from the target object (i.e., echo signals) to thereby form ultrasound data corresponding to a plurality of frames $F_i$, wherein $1 \leq i \geq N$. Hereinafter, one embodiment will describe a fetus as the target object. However, the target object may not be limited thereto.

Figure 2:
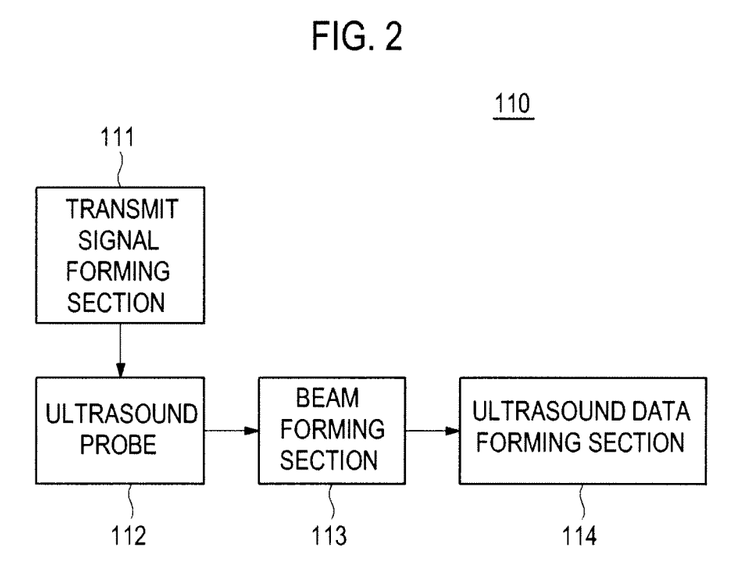
FIG. 2 is a block diagram showing an illustrative embodiment of an ultrasound data acquisition unit.

FIG. 2 is a block diagram showing an illustrative embodiment of the ultrasound data acquisition unit 110. The ultrasound data acquisition unit 110 may include a transmit signal forming section 111, an ultrasound probe 112 containing a plurality of transducer elements (not shown), a beam forming section 113 and an ultrasound data forming section 114.

Figure 3:
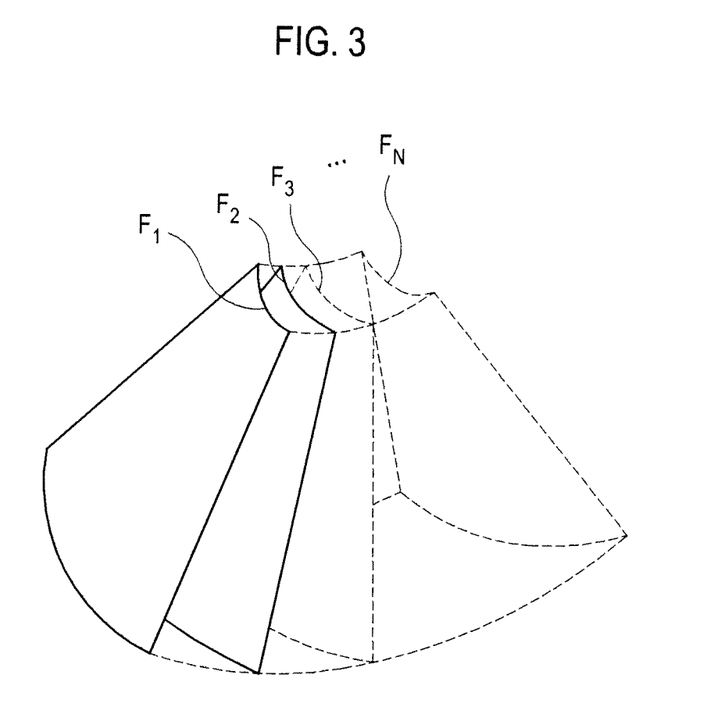
FIG. 3 is a schematic diagram showing an example of obtaining frames.

The transmit signal forming section 111 may be operable to produce transmit signals in consideration of positions of the transducer elements and predetermined focal points for forming a plurality of frames $F_i$, wherein $1 \leq i \geq N$, as shown in FIG. 3. Although the frames $F_i$ are illustrated in a fan shape in FIG. 3, the shape of the frames $F_i$ may not be limited thereto. The frames $F_i$ may include brightness mode image frames.

The ultrasound probe 112, which is coupled to the transmit signal forming section 111, may be operable to receive the transmit signals from the transmit signal forming section 111 and convert them into ultrasound signals, which may travel into the target object. The ultrasound probe 112 may be further operable to receive echo signals reflected from the target objet to thereby form receive signals. The ultrasound probe 112 may include a 3-dimensional probe, a 2-dimensional array probe and the like.

The beam forming section 113, which is coupled to the ultrasound probe 112, may be operable to digitize the receive signals to obtain digital receive signals. The beam forming section 113 may be further operable to apply delays to the digital receive signals in consideration of positions of the transducer elements and the focal points to thereby form receive-focused beams.

The ultrasound data forming section 114, which is coupled to the beam forming section 113, may be operable to form ultrasound data indicative of the target object by using the receive-focused beams. Further, the ultrasound data forming section 114 may be operable to perform a variety of signal processing such as gain adjustment, filtering, etc., upon the receive-focused beams.

Referring back to FIG. 1, the user input unit 120 may receive input information. The input information may include information on setup of reference planes ("reference plane setup information"). The user input unit 120 may be embodied with a control panel, a mouse, a key board and the like.

The processor 130 may be operable to form volume data by using the ultrasound data provided from the ultrasound data acquisition unit 110. Further, the processor 130 may be operable to set multiple sectional planes in the volume data and form multiple plane images corresponding to the respective section planes.

Figure 4:
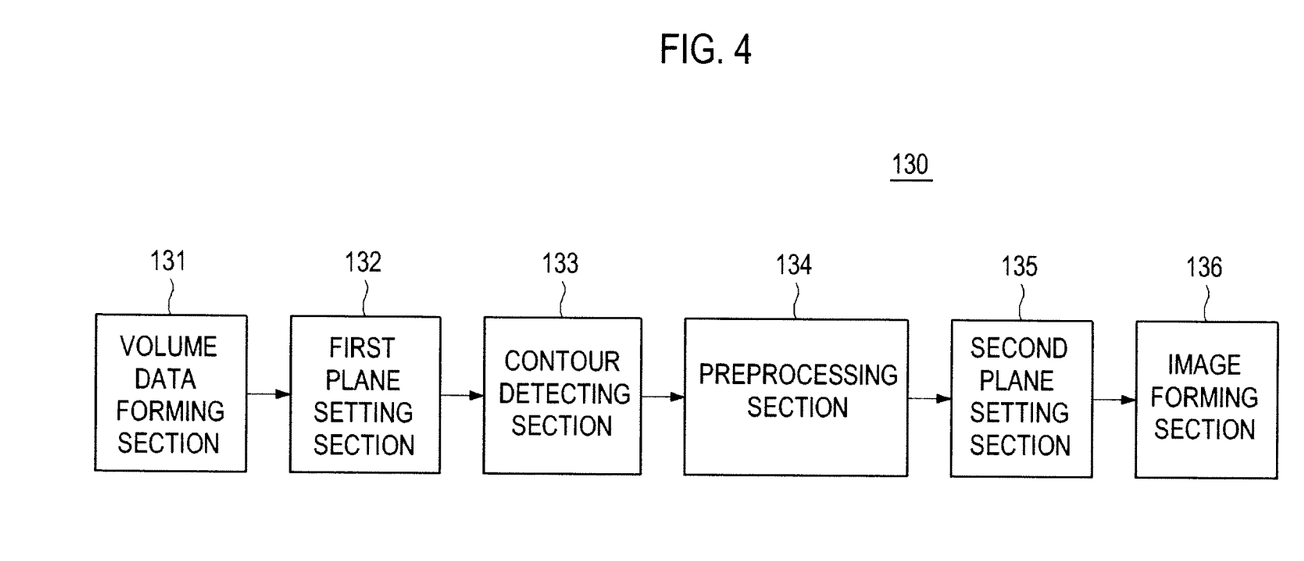
FIG. 4 is a block diagram showing an illustrative embodiment of a processor.

FIG. 4 is a block diagram showing an illustrative embodiment of the processor 130. The processor 130 may include a volume data forming section 131, a first plane setting section 132, a contour detecting section 133, a preprocessing section 134, a second plane setting section 135 and an image forming section 136.

Figure 5:
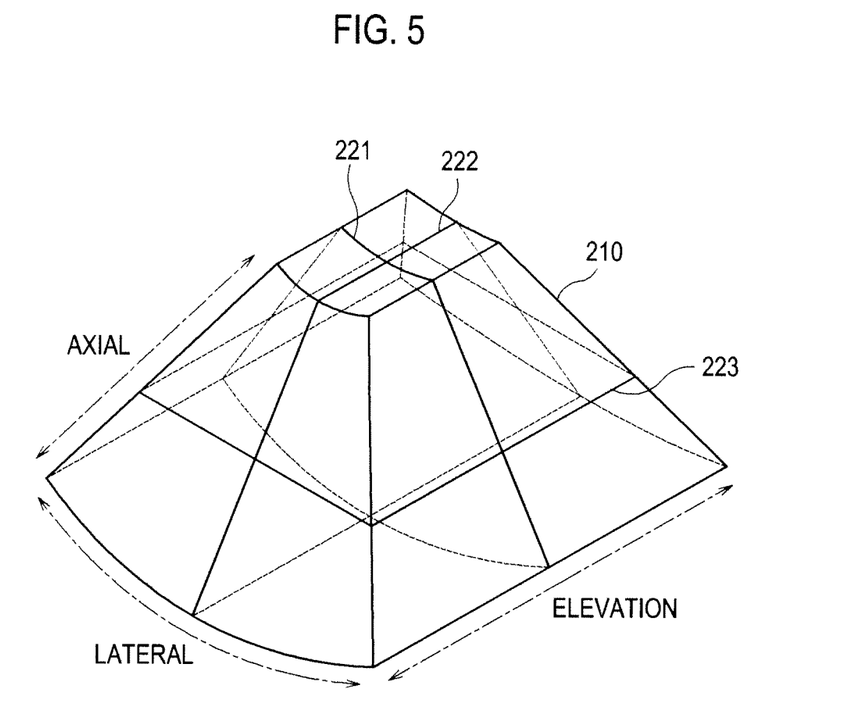
FIG. 5 is a schematic diagram showing an example of volume data.

The volume data forming section 131 may be operable to form volume data 210 by using the ultrasound data, which are provided from the ultrasound data acquisition unit 110, as shown in FIG. 5. The volume data may include a plurality of voxels each having a brightness value. In FIG. 5, numeral references 221-223 may represent a sagittal view, a coronal view and an axial view, respectively, which are perpendicular to each other. Also, in FIG. 5, an axial direction may represent a propagation direction of the ultrasound signals from a scan head of the ultrasound probe 112, a lateral direction may represent a scanning direction of scan lines, which may be a longitudinal direction of the transducer elements, and an elevation direction may represent a swing direction of the transducer elements, which may be a depth direction in a 3-dimensional ultrasound image.

The first plane setting section 132 may be operable to set a reference plane in the volume data 210. In one embodiment, the first plane setting section 132 may be operable to set the reference plane in response to the reference plane setup information, which may be inputted through the user input unit 130. The reference plane may be a transthalamic plane associated with the axial view ("first transthalamic plane").

The contour detecting section 133 may be operable to detect a falx contour in the reference plane. The falx is dura mater for separating cerebral hemispheres. The contour detecting section 133 may be further operable to detect a contour of a cerebrum in the reference plane. Further, the contour detection section 133 may be operable to detect an entire contour of a fetal brain in the volume data. The contour detection may be achieved by using an edge mask such as Sobel, Prewitt, Robert, Canny or the like. Also, the contour may be detected based on eigenvalue differences using an edge structure tensor.

Figure 6:
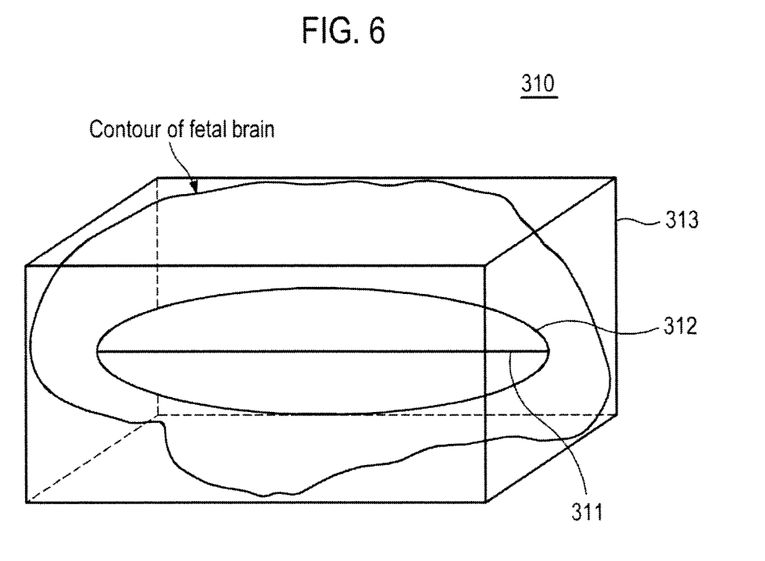
FIG. 6 is a diagram showing an illustrative embodiment of a graphic guide.

The preprocessing section 134 may be operable to normalize the volume data by using the falx contour, the cerebrum contour and the entire contour of the fetal brain, which are detected on the contour detecting section 133. In one embodiment, the preprocessing unit 134 may be operable to apply normalization reference data to the volume data for normalization thereof. The normalization reference data may include a graphic guide 310, as shown in FIG. 6. The graphic guide 310 may include a first guide line 311 for matching with the falx contour, a second guide line 312 for matching with the cerebrum contour and a third guide line 313 for matching with the entire contour of the fetal brain.

More particularly, the preprocessing section 134 may be operable to match the first guide line 311 in the graphic guide 310 with the falx contour in the reference plane. While the first guide line 311 is matched with the falx contour, the preprocessing section 134 may be operable to compare the second guide line 312 with the cerebrum contour and adjust a size of the volume data to match the cerebrum contour with the second guide line 312. For example, the preprocessing section 134 may be operable to compare the second guide line 312 with the cerebrum contour. If it is determined that the cerebrum contour exceeds the second guide line 312 in at least one of axial, lateral and elevation directions, then the preprocessing section 134 may adjust the size of the volume data in the corresponding direction (i.e., reduction). On the other hand, if it is determined that the cerebrum contour is smaller than the second guide line 312 in at least one of axial, lateral and elevation directions, then the preprocessing section 134 may adjust the size of the volume data in the corresponding direction (i.e., enlargement).

The preprocessing section 134 may be further operable to compare the third guide line 313 with the entire contour of the fetal brain and adjust the size of the volume data for matching with the third guide line 313 while the second guide line 312 is matched with the cerebrum contour. For example, if it is determined that the entire contour of the fetal brain exceeds the third guide line 313 in an axial direction, then the preprocessing section 134 may adjust the size of the volume data in the axial direction (i.e., reduction). On the other hand, if it is determined that the entire contour of the fetal brain is smaller than the third guide line 313 in an axial direction, then the preprocessing section 134 may adjust the size of the volume data in the axial direction (i.e., enlargement).

Figure 7:
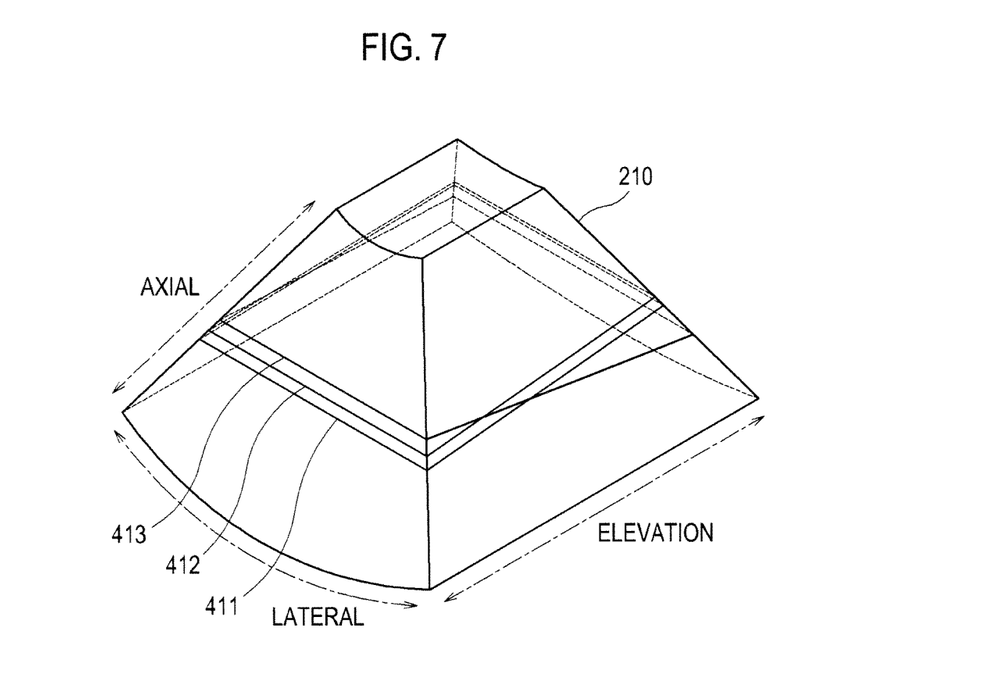
FIG. 7 is a schematic diagram showing an illustrative embodiment of setting a first transthalamic plane, a transventricular plane and a first trancerebellar plane as axial views.

The second plane setting section 135 may be operable to set a first transthalamic plane, a transventricular plane and a first transcerebellar plane with respect to the reference plane in the normalized volume data 230 as axial views. In one embodiment, the second plane setting section 135 may set the first transthalamic plane at an identical location to the reference plane, as shown in FIG. 7. The second plane setting section 135 may move the reference plane in the normalized volume data 230 in parallel to a first predetermined location to set the transventricular plane 412. That is, the transventricular plane 412 is set at the first predetermined location, which is spaced away from the first transthalamic plane 411 in parallel at a predetermined distance. The second plane setting section 135 may be operable to rotate the reference plane at a first predetermined angle with respect to the transthalamic plane 411 to thereby set the first transcerebellar plane 413. That is, the first transcerebellar plane 413 may be set at the location, which is rotated at the first predetermined angle with respect to the first transthalamic plane 411.

Figure 8:
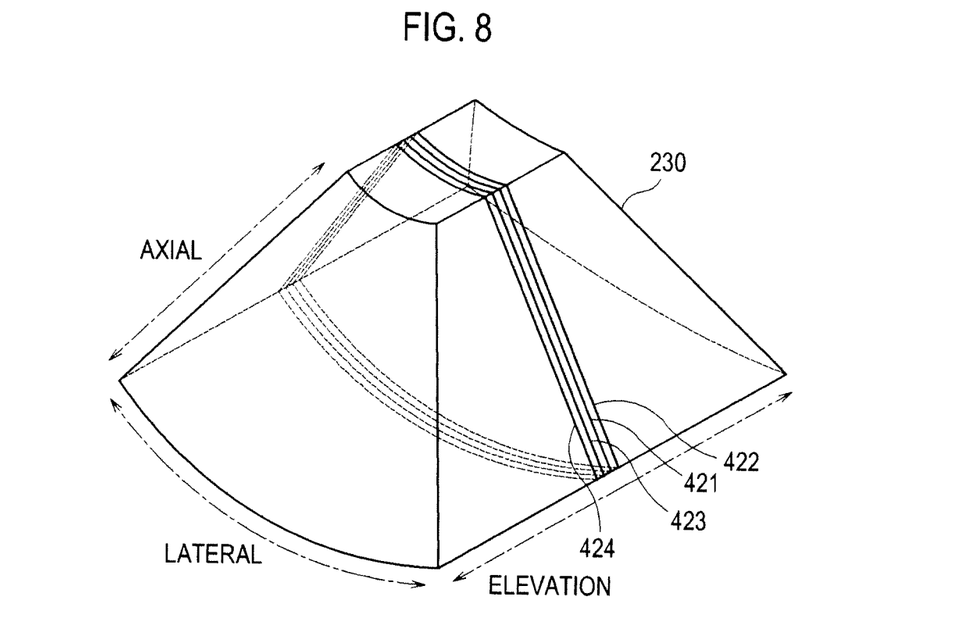
FIG. 8 is a schematic diagram showing an illustrative embodiment of setting a second transthalamic plane, a second transcerebellar plane, a transcaudate plane and a transfrontal plane as coronal views.

The second plane setting section 135 may be operable to set a second transthalamic plane, a second transcerebellar plane, a transcaudate plane and a transfrontal plane with respect to the first transthalamic plane 411 in the normalized volume data 230 as coronal views, as shown in FIG. 8. In one embodiment, the second plane setting section 135 may be operable to rotate the reference plane perpendicularly in an axial direction with respect to the first transthalamic plane 411 in the normalized volume data 230 and rotate the reference plane, which is perpendicularly rotated, at a second predetermined angle to thereby set the second transthalamic plane 421. That is, the second transthalamic plane 421 may be set at a location, which is rotated at a predetermined angle (90°—second predetermined angle) with respect to the first transthalamic plane 411.

The second plane setting section 135 may be operable to move the reference plane in parallel to a second predetermined location, which is spaced away from the second transthalamic plane 421 in the normalized volume data 230 by a predetermined distance to thereby set the second transcerebellar plane 422. That is, the second transcerebellar plane 422 may be set at the second location, which is spaced away from the second transthalamic plane 421 in parallel.

The second plane setting section 135 may be operable to move the reference plane in parallel to a third predetermined location, which is spaced away from the second transthalamic plane 421 in the normalized volume data 230 by a predetermined distance to thereby set the transcaudate plane 423. That is, the transcaudate plane 423 may be set at the third predetermined location, which is spaced away from the second transthalamic plane 421 in parallel.

The second plane setting section 135 may be operable to move the reference plane in parallel to a fourth predetermined location, which is spaced away from the second transcaudate plane 423 in the normalized volume data 230 by a predetermined distance to thereby set the transfrontal plane 424. That is, the transfrontal plane 424 may be set at the fourth predetermined location, which is spaced away from the second transcaudate plane 423 in parallel.

Figure 9:
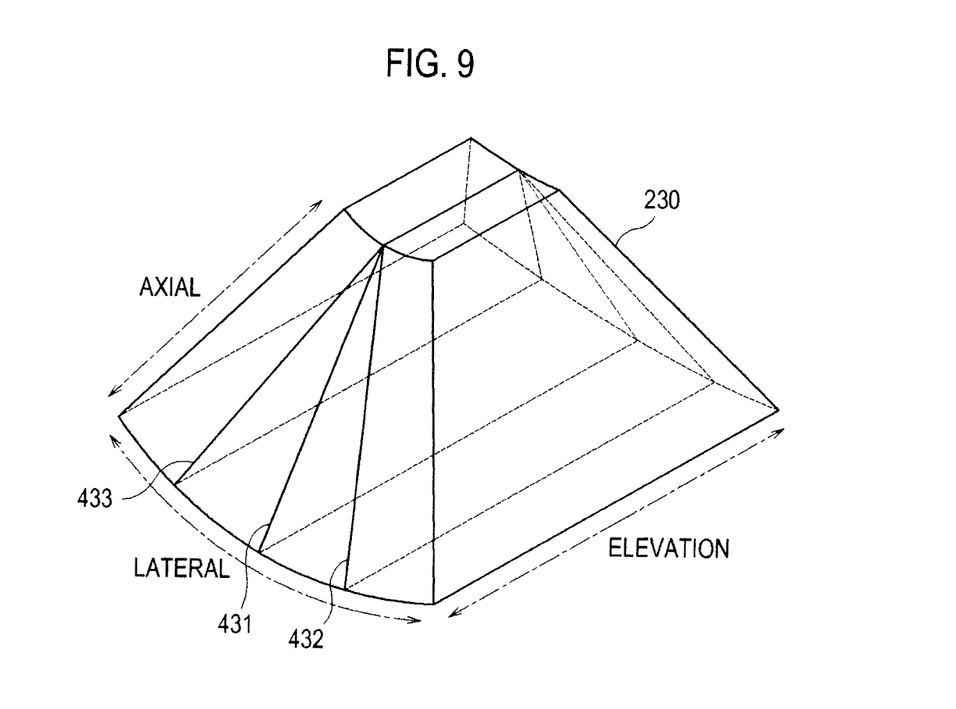
FIG. 9 is a schematic diagram showing an illustrative embodiment of setting a midsagittal plane, a left parasagittal plane and a right parasagittal plane as sagittal views.

The second plane setting section 135 may be operable to set a midsagittal plane, a left parasagittal plane and a right parasagittal plane with respect to the first transthalamic plane. In one embodiment, the second plane setting section 135 may be operable to rotate the reference plane perpendicularly with respect to the first transthalamic plane 411 in the normalized volume data 230 to thereby set the midsagittal plane 431, as shown in FIG. 9. The second plane setting section 135 may be operable to rotate the reference plane at a third predetermined angle with respect to the midsagittal plane 431 to thereby set the left parasagittal plane 432. That is, the left parasagittal plane 432 may be set at a location, which is rotated at the third predetermined angle with respect to the midsagittal plane 431. The second plane setting section 135 may be operable to rotate the reference plane at a fourth predetermined angle with respect to the midsagittal plane 431 to thereby set the right parasagittal plane 433. That is, the right parasagittal plane 433 may be set at a location, which is rotated at the fourth predetermined angle with respect to the midsagittal plane 431 and which is rotated at an angle (third predetermined angle+fourth predetermined angle) with respect to the left parasagittal plane 432.

The image forming section 136 may be operable to form plane images corresponding to the respective multiple planes, which are set in the second plane setting section 135, i.e., the first transthalamic plane 411, transventricular plane 412, the first transcerebellar plane 413, the second transthalamic plane 421, the second transcerebellar plane 422, the second transcaudate plane 423, the transfrontal plane 424, the midsagittal plane 431, the left parasagittal plane 432 and the right parasagittal plane 433. The image forming section 136 may be further operable to perform rendering upon the volume data to form a 3-dimensional ultrasound image.

Referring back to FIG. 1, the display unit 140 may display the multiple plane images provided from the processor 130. In one embodiment, the multiple plane images may be displayed with being classified by views. Also, the plane image of the first transthalamic plane, which is matched with the graphic guide, may be displayed with other plane images. Further, the display unit 140 may display the 3-dimensional ultrasound image.

Although embodiments have been described with reference to a number of illustrative embodiments thereof, it should be understood that numerous other modifications and embodiments can be devised by those skilled in the art that will fall within the scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound data acquisition unit configured to transmit/receive ultrasound signals to/from a target object including a fetal brain to form ultrasound data; and
   a processor configured to form volume data indicative of the target object by using the ultrasound data, the processor including:
   a first plane setting section configured to set a reference plane containing a falx and a cerebrum in the volume data;
   a contour detecting section configured to detect a contour of the falx and a contour of the cerebrum in the reference plane and an entire contour of the fetal brain in the volume data;
   a preprocessing section configured to adjust a size of the volume data and normalize the volume data, by using normalization reference data corresponding to the falx contour, the cerebrum contour and the entire contour of the fetal brain; and a second plane setting section configured to set multiple planes with respect to the reference plane in the normalized volume data, wherein the processor is further configured to form plane images corresponding to respective ones of the multiple planes by using the normalized volume data.

2. The ultrasound system of claim 1, wherein the processor further includes a volume data forming section configured to form the volume data.

3. The ultrasound system of claim 1, further comprising a user input unit configured to receive input information to set the reference plane in the volume data.

4. The ultrasound system of claim 1, wherein the normalization reference data include a first guide line for matching with the falx contour, a second guide line for matching with the cerebrum contour and a third guide line for matching with the entire contour of the brain.

5. The ultrasound system of claim 4, wherein the preprocessing section is configured to determine whether the cerebrum contour exceeds the second guide line, and when it is determined that the cerebrum contour exceeds the second guide line in at least one of axial, lateral and elevation directions, the preprocessing section is configured to adjust the size of the volume data by reducing the size of the volume data in the at least one of axial, lateral and elevation directions.

6. The ultrasound system of claim 1, wherein the second plane setting section is configured to:

set a first transthalamic plane at a location of the reference plane in the normalized volume data;

move the reference plane in the normalized volume data to a first predetermined location to set the transventricular plane; and rotate the reference plane at a first predetermined angle with respect to the transthalamic plane to thereby set a first transcerebellar plane in the normalized volume data as axial views.

7. The ultrasound system of claim 6, wherein the second plane setting section is further configured to:

rotate the reference plane perpendicularly in a first direction with respect to the first transthalamic plane in the normalized volume data and then rotate the perpendicularly-rotated reference plane at a second predetermined angle to thereby set a second transthalamic plane;

move the reference plane to a second predetermined location with respect to the second transthalamic plane in the normalized volume data to thereby set a second transcerebellar plane;

move the reference plane to a third predetermined location with respect to the second transthalamic plane in the normalized volume data to thereby set a first transcaudate plane; and move the reference plane to a fourth predetermined location with respect to a second transcaudate plane in the normalized volume data to thereby set the transfrontal plane, as coronal views.

8. The ultrasound system of claim 7, wherein the second plane setting section is further configured to:

rotate the reference plane perpendicularly with respect to the first transthalamic plane in the normalized volume data to thereby set the midsagittal plane;

rotate the reference plane at a third predetermined angle with respect to the midsagittal plane to thereby set the left parasagittal plane; and rotate the reference plane at a fourth predetermined angle with respect to the midsagittal plane to thereby set the right parasagittal plane.

9. A method of providing multiple plane images for a target object including a fetal brain in an ultrasound system, comprising:

a) forming volume data indicative of a target object including a fetal brain;

b) setting a reference plane containing a falx and a cerebrum in the volume data;

c) detecting a contour of the falx and a contour of the cerebrum in the reference plane and an entire contour of the fetal brain in the volume data;

d) adjusting a size of the volume data and normalizing the volume data by using normalization reference data corresponding to the falx contour, the cerebrum contour and the entire contour of the fetal brain;

e) setting multiple planes with respect to the reference plane in the normalized volume data; and f) forming plane images corresponding to respective ones of the multiple planes by using the normalized volume data.

10. The method of claim 9, further comprising inputting information to set the reference plane in the volume data.

11. The method of claim 9, wherein the normalization reference data include a first guide line for matching with the falx contour, a second guide line for matching with the cerebrum contour and a third guide line for matching with the entire contour of the brain.

12. The method of claim 11, further comprising:

determining whether the cerebrum contour exceeds the second guide line, wherein the adjusting the size of the volume data includes reducing, when it is determined that the cerebrum contour exceeds the second guide line in at least one of axial, lateral and elevation directions, adjusting the size of the volume data, the size of the volume data in the at least one of axial, lateral and elevation directions.

13. The method of claim 9, wherein the step e) includes:

setting a first transthalamic plane at a location of the reference plane in the normalized volume data;

moving the reference plane in the normalized volume data to a first predetermined location to set the transventricular plane; and rotating the reference plane at a first predetermined angle with respect to the transthalamic plane to thereby set a first transcerebellar plane in the normalized volume data, as axial views.

14. The method of claim 13, wherein the step e) further includes:

rotating the reference plane perpendicularly in a first direction with respect to the first transthalamic plane in the normalized volume data and then rotating the perpendicularly-rotated reference plane at a second predetermined angle to thereby set a second transthalamic plane;

moving the reference plane to a second predetermined location with respect to the second transthalamic plane in the normalized volume data to thereby set a second transcerebellar plane;

moving the reference plane to a third predetermined location with respect to the second transthalamic plane in the normalized volume data to thereby set a first transcaudate plane; and moving the reference plane to a fourth predetermined location with respect to a second transcaudate plane in the normalized volume data to thereby set the transfrontal plane, as coronal views.

15. The method of claim 14, wherein the step e) further includes:
- rotating the reference plane perpendicularly with respect to the first transthalamic plane in the normalized volume data to thereby set the midsagittal plane;
- rotating the reference plane at a third predetermined angle with respect to the midsagittal plane to thereby set the left parasagittal plane; and
- rotating the reference plane at a fourth predetermined angle with respect to the midsagittal plane to thereby set the right parasagittal plane.

* * * * *